United States Patent [19]

Farnand et al.

[11] Patent Number: 4,759,850
[45] Date of Patent: Jul. 26, 1988

[54] MEMBRANE PROCESS FOR SEPARATING METHANOL FROM METHANOL/HYDROCARBON SOLUTIONS

[75] Inventors: Brian A. Farnand; Henry Sawatzky, both of Ottawa, Canada

[73] Assignee: Energy, Mines and Resources Canada, Ottawa, Canada

[21] Appl. No.: 2,195

[22] Filed: Jan. 12, 1987

[51] Int. Cl.⁴ ............................................. B01D 13/00
[52] U.S. Cl. ................................... 210/654; 210/655
[58] Field of Search ............... 210/652, 653, 654, 655, 210/651

[56] References Cited

U.S. PATENT DOCUMENTS

| | | | |
|---|---|---|---|
| 2,970,468 | 2/1961 | Price | 210/649 |
| 3,228,877 | 1/1966 | Mahon | 210/638 |
| 3,320,328 | 5/1967 | Michaels | 210/644 |
| 3,410,794 | 11/1968 | Li | 210/643 |
| 3,853,756 | 12/1974 | Stana | 210/412 X |
| 3,919,075 | 11/1975 | Parc et al. | 210/644 |
| 3,977,967 | 8/1976 | Trulson et al. | 210/651 |
| 3,990,963 | 11/1976 | Audibert et al. | 208/179 |
| 4,229,297 | 10/1980 | Nohmi et al. | 210/654 |
| 4,326,960 | 4/1982 | Iwahori et al. | 210/652 |
| 4,411,790 | 10/1983 | Arod et al. | 210/651 |
| 4,499,117 | 2/1985 | Bonneau | 210/652 |

OTHER PUBLICATIONS

Sourirajan, S., Editor, *Reverse Osmosis and Synthetic Membranes*, Nat. Res. Con. Canada, NRCC No. 15627, 1977, pp. 201–202.

*Primary Examiner*—Ivars Cintins

[57] ABSTRACT

A reverse osmosis process is described for removing alcohols from hydrocarbons, in the additional presence of ethers. Depending on the nature of the membrane used, the methanol can be selectively removed as the membrane permeate or retained as the membrane concentrate. The membrane may be made from cellulose esters, polyethylene, polyvinylchloride, polyvinylidene chloride-polyvinyl chloride, etc.

5 Claims, 1 Drawing Sheet

MEMBRANE PROCESS FOR SEPARATING METHANOL FROM METHANOL/HYDROCARBON SOLUTIONS

This invention relates to a separation process for removing alcohols from hydrocarbons, particularly in the presence of ethers, utilizing a reverse osmosis membrane.

Distillation is a common method for separating components in solution based on their vapour pressure. In cases where the components have similar vapour pressures, other separation methods such as extraction and absorption must be used. These alternative methods require large capital investments and large operating costs. One such method is the separation of alcohols from hydrocarbons where azeotropes are commonly encountered. For example, the manufacture of ethers for blending with gasoline as an octane enhancing agent requires the separation of various amounts of methanol from the final product to protect the catalyst used in subsequent reactions, to meet fuel quality specifications for vapour pressure, corrosion and miscibility, and for enhanced manufacture by recycling unreacted components. Because methanol and saturated hydrocarbons from azeotropes that cannot be resolved by distillation, other methods such as liquid-liquid extraction, gas-liquid absorption and liquid-solid adsorption on resins are being used to remove the alcohol. An operational difficulty of these two separation processes is their apparent failure to selectively separate methanol from solutions that contain other polar solvents such as ethers when in the presence of hydrocarbons. This presents an additional burden to the separation process by requiring a preliminary separation of the ethers from the hydrocarbons, usually by distillation despite the methanol azeotrope, followed by the independent treatment of the hydrocarbon-methanol and ether-methanol mixtures.

Reverse osmosis is a widely used technique for separating components which are difficult to separate by techniques such as distillation. Osmosis occurs when two solutions of different concentrations in the same solvent are separated from one another by a membrane. If the membrane is ideally semi-permeable, that is, if it is permeable to the solvent and not to the solute, then a flow of solvent occurs from the more dilute into the more concentrated solution. This continues until the two solutions become equal in concentration or until the pressure in the chamber of the more concentrated solution rises to a certain well-defined value. The pressure difference at which no flow occurs is termed the osmotic pressure difference between the two solutions. If a pressure in excess of this osmotic pressure difference is applied to the more concentrated solution, then the solvent can be caused to flow into the dilute solution. The name "reverse osmosis" is used to describe this process. A typical reverse osmosis system is described in U.S. Pat. No. 3,853,756.

SUMMARY OF THE INVENTION

This invention utilizes the reverse osmosis technique for the selective removal of methanol from methanol/hydrocarbon solutions, particularly in the presence of other polar solvents, such as ethers and aromatic hydrocarbons. Depending on the nature of the membrane used, it has been found that the methanol can be selectively removed as the membrane permeate or it may be retained as the membrane retentate.

In the process of the invention, methanol is separated from a non-aqueous miscible solution of methanol, hydrocarbons and ethers by filtering the solution through a semi-permeable membrane having a feed side and a permeate side, with a higher pressure on the feed side of the membrane than on the permeate side. The materials permeating the membrane and the materials retained by the membrane on the feed side are then collected.

The reverse osmosis technique is, of course, based upon the relative affinity of the components in solution for the reverse osmosis membrane surface and on their molecular size and shape. The affinity is determined by the interaction of the chemical properties of the components and the functional groups presented by the membrane surface. Because of the diverse nature of the components, a suitable membrane can be chosen that will selectively permeate the polar components or the less polar components. Both cases have two product streams; one rich in methanol and the other lean in methanol. The methanol-rich stream can be recycled to the etherification reactor. The methanol lean stream can be distilled to separate the hydrocarbons and the ethers, provided the methanol content has been reduced to below the process specification limits. If the level remains too high, it can be passed through several membrane separations as required to make the necessary separations. Methanol-rich streams can be recycled to the etherification reactor or to subsequent operations. The ultimate process design depends on product methanol content specifications, downstream process specifications, membrane type, and the composition and concentration of the original feed solution.

The reverse osmosis membrane is usually made from such materials as cellulose or cellulose esters such as cellulose acetate, cellulose acetate-butyrate, polyethylene, polyvinylchloride, polyvinylidene chloride-polyvinyl chloride, etc.

BRIEF DESCRIPTION OF THE DRAWINGS

For a better understanding of the invention, reference may be made to the preferred embodiments exemplary of the invention, shown in the accompaying drawings, in which.

DESCRIPTION OF THE PREFERRED EMBODIMENTS

Figure 1:
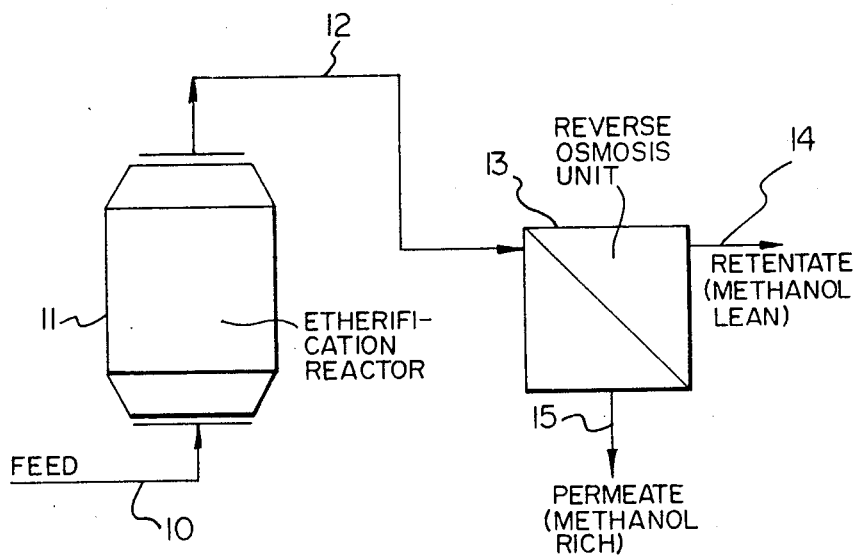
FIG. 1 is a schematic diagram of one embodiment of the method of the invention with methanol in the permeate.

As will be seen from the drawings, a feedstock 10 typically comprising methanol, olefins and hydrocarbons is fed into an etherification reactor 11 to form ethers for blending with gasoline. The product stream 12 from the reactor 11 comprises methanol, olefins, hydrocarbons and the desired ether. This product stream is fed into a reverse osmosis unit containing a selected membrane and from reverse osmosis unit 13 is obtained a retentate stream 14 and a permeate stream 15.

EXAMPLE 1

Figure 2:
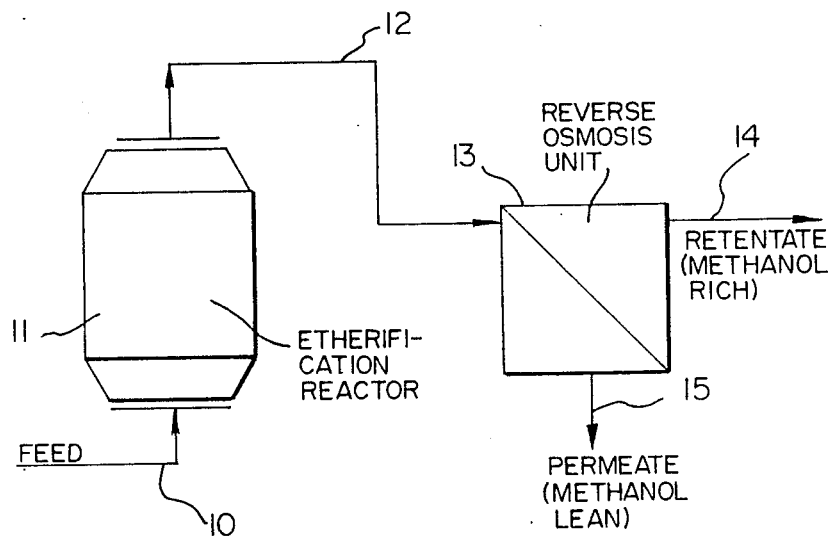
FIG. 2 is a schematic diagram of a further embodiment of the method of this invention showing the methanol in the retentate.

A system of the type shown in FIG. 2 was used containing a small pore polyvinyl chloride membrane. This was used as a static reverse osmosis cell without agitation and a nominal 1% methanol in pentane solution was passed through the reverse osmosis cell. This was done at room temperature and nitrogen pressures from 1 to 6.5 MPa. The permeate and liquid on the high pressure side of the membrane (retentate) in the static cell were collected and analyzed for methanol concentration. The permeation rate of the membrane was also measured. The results obtained are shown in Table 1 below:

TABLE 1

| Membrane | Nominal conc. % | Pressure MPa | Permeation rate $g \cdot h^{-1} m^{-2} \times 10^3$ | Separation* factor for methanol |
|---|---|---|---|---|
| 1 | 1.0 | 1.0 | 19.95 | 0.56 |
| 2 | 1.0 | 1.5 | 25.61 | 0.91 |
| 3 | 1.0 | 2.0 | 33.19 | 0.89 |
| 4 | 5.0 | 1.0 | 11.23 | 0.71 |
| 5 | 1.0 | 4.0 | 1.98 | 0.54 |
| 6 | 1.0 | 5.0 | 1.27 | 0.36 |
| 7 | 1.0 | 5.0 | 1.13 | 0.54 |
| 8 | 1.0 | 5.0 | 2.33 | 0.78 |
| 9 | 1.0 | 6.5 | 11.24 | 0.77 |

*$\dfrac{\text{mol. fraction methanol in permeate/total mols in permeate}}{\text{mol. fraction methanol in feed/total mols in feed}}$ It will be seen from the above table that the permeate was depleted in methanol by the membrane in all tests.

EXAMPLE 2

A cellulose acetate-butyrate (CAB) membrane was prepared from a casting solution containing 10 parts CAB, 20 parts acetone, 8 parts formamide and 4 parts maleic acid. The film was cast at $-10°$ C., evaporated for 30 seconds, subjected to gelation in water and preshrunk in hot water at 90° C. for 3 minutes.

The cellulose acetate-butyrate membrane was used in the system of FIG. 1 to separate a nominal 1% methanol in pentane soluble. Pressures were varied from 5 to 10 MPa at ambient temperature in a static cell. The permeate and the retentate were collected and analyzed and the permeation rate was measured. Results for several of these membranes are shown in Table 'below and it will be noted that this membrane selectively permeated methanol.

TABLE 2

| Membrane | Pressure MPa | Permeation rate $g \cdot h^{-1} \cdot m^{-2} \times 10^3$ | Separation factor for methanol |
|---|---|---|---|
| 1 | 5.0 | 1.59 | 1.37 |
| 2 | 5.0 | 0.19 | 1.17 |
| 3 | 6.0 | 2.38 | 1.27 |
| 4 | 7.0 | — | 1.27 |
| 5 | 7.0 | 2.31 | 1.33 |
| 6 | 8.0 | 3.94 | 1.49 |
| 7 | 8.0 | 1.31 | 1.67 |
| 8 | 8.0 | 1.30 | 1.43 |
| 9 | 9.0 | 2.80 | 1.48 |
| 10 | 10.0 | 1.67 | 1.42 |

EXAMPLE 3

Thin commercial packaging films of various materials were used to separate a nominal 1% methanol in pentane solution. The films had thicknesses in the range of about 0.01 to 0.02 mm. These membranes were used in the same type of device as shown in FIGS. 1 and 2 and the operating conditions and results obtained are shown in Table 3 below.

TABLE 3

| Membrane | Pressure MPa | Permeation rate (kg h$^{-1}$ m$^{-2}$) | Weight % Retentate methanol/pentane | Weight % Permeate methanol/pentane | Separation factor for methanol |
|---|---|---|---|---|---|
| Glad Wrap | 6.0 | 1.37 | 0.27/99.73 | 0.28/99.72 | 1.04 |
| Stretch & Seal | 5.5 | * | 0.28/99.72 | 0.27/99.73 | 0.96 |
| Saran Wrap | 8.0 | 44.26 | 0.34/99.66 | 0.11/99.89 | 0.32 |
| Stretch & Seal | 8.0 | 6.56 | 0.26/99.74 | 0.2/99.73 | 1.02 |

Glad Wrap is a trademark of Union Carbide for film containing polyethylene and polyvinyl acetate.
Stretch & Seal is a trademark of Imperial Oil for film containing polyvinyl chloride and chlorinated polyethylene.
Saran Wrap is a trademark of Dow Chemical for film containing polyvinylidene chloride and polyvinyl chloride.
*not measured

EXAMPLE 4

For this test, an artifical etherification reactor effluent stream was prepared. The feed solution, which was placed on the high pressure side of the membrane, consisted of 11% methanol, 15% 2-methyl-2-butene, 67% pentane and 7% ether. The ether was either methyl tertiary butyl ether (MTBE) or tertiary amyl methyl ether (TAME). Pressures were varied from 4 to 10 MPa at ambient temperature. Table 4 shows the separation factors obtained and it will be seen that both selective permeation and methyl rejection can be obtained. Four different membranes were used, these being polyethylene (PE), polyethylene and polyvinyl acetate (PE+PVAC), cellulose acetate (CA) and cellulose acetate-butyrate (CAB). In the case of cellulose acetate-butyrate, almost no change occurs in the ether content of the feed compared with permeate.

TABLE 4

| Membrane | Ether in mixture | No. of experiments | Average separation factor for Methanol/ether/Pentane/2-M-2-butene |
|---|---|---|---|
| PE | MTBE | 2 | 0.41/0.84/1.56/1.19 |
| | TAME | 2 | 0.81/0.90/1.14/1.04 |
| PE + PVAC | MTBE | 8 | 0.32/0.83/1.91/1.29 |
| | TAME | 4 | 0.41/0.83/1.79/1.21 |
| CA | MTBE | 3 | 9.54/0.63/0.38/0.58 |
| | TAME | 6 | 11.27/0.36/0.32/0.55 |
| CAB | MTBE | 5 | 2.37/1.03/0.64/0.83 |
| | TAME | 8 | 2.33/0.94/0.66/0.88 |

EXAMPLE 5

This test was conducted in a circulated reverse osmosis test cell with a variety of different membranes, all membranes being tested with the same solution and for the same time period. The operating conditions and results obtained are shown in Table 5. Results are shown both for the case of methanol and hydrocarbons with only a trace of TAME and where TAME is present in quantities typical of a commercial etherification reactor product.

TABLE 5

| Membrane | Pressure* MPa | Concn. Feed wt. % MeOH | nC$_5$ | TAME | Concn. Perm wt. % MeOH | nC$_5$ | TAME | g/h/13.3 cm$^2$ Permeation rate | Separation Factor, mol fr basis MeOH | nC$_5$ | TAME |
|---|---|---|---|---|---|---|---|---|---|---|---|
| CA 2 | 2.00 | 4.38 | 94.72 | 0.08 | 27.22 | 72.06 | 0.13 | 0.62 | 8.166 | 0.130 | 1.244 |
| CA 3 | | | | | 32.20 | 67.20 | 0.12 | 0.54 | 10.368 | 0.103 | 1.127 |
| CAB 4 | | | | | 9.16 | 89.98 | 0.14 | 3.93 | 2.201 | 0.471 | 1.612 |
| CA 5 | | | | | 41.15 | 58.24 | 0.11 | 0.46 | 15.267 | 0.0699 | 0.931 |
| PE | | | | | 3.33 | 95.74 | 0.15 | 0.88 | 0.752 | 1.296 | 1.873 |
| PE + PVAC | 2.00 | 10.54 | 83.41 | 5.46 | 5.33 | 88.16 | 5.74 | 0.72 | 0.478 | 1.782 | 1.122 |
| CA 2 | | | | | 31.27 | 62.25 | 5.96 | 0.84 | 3.892 | 0.279 | 0.883 |
| CA 3 | | | | | 30.30 | 63.97 | 5.11 | 0.88 | 3.713 | 0.298 | 0.760 |
| CAB 4 | | | | | 15.12 | 80.29 | 3.96 | 4.54 | 1.506 | 0.723 | 0.680 |
| CA 5 | | | | | 36.61 | 56.89 | 6.02 | 0.66 | 4.953 | 0.220 | 0.850 |
| PE | | | | | 6.45 | 88.84 | 4.01 | 0.60 | 0.582 | 1.667 | 0.760 |
| PE + PVAC | 2.00 | 9.57 | 84.56 | 5.21 | 5.22 | 89.10 | 4.94 | 0.84 | 0.520 | 1.712 | 0.997 |
| CA 2 | | | | | 37.36 | 56.26 | 5.89 | 0.73 | 5.697 | 0.193 | 0.851 |
| CA 3 | | | | | 30.49 | 63.03 | 6.07 | 0.86 | 4.180 | 0.262 | 0.941 |
| CAB 4 | | | | | 11.41 | 81.52 | 6.41 | 5.10 | 1.222 | 0.808 | 1.217 |
| CA 5 | | | | | 37.90 | 54.50 | 7.11 | 0.75 | 5.868 | 0.183 | 1.038 |
| PE | | | | | 6.90 | 85.34 | 7.12 | — | 0.704 | 1.233 | 1.437 |

*23° C. operating temp.

We claim:

1. A process for separating methanol from a non-aqueous miscible solution of methanol, hydrocarbons and ethers which comprises filtering the solution through a semi-permeable membrane having a feed side and a permeate side with a higher pressure on the feed side of the membrane than on the permeate side and collecting the materials permeating the membrane and the materials retained by the membrane.

2. A process according to claim 1 wherein a membrane is used through which the methanol passes.

3. A process according to claim 2 wherein the membrane is made of cellulose acetate or cellulose acetate-butyrate.

4. A process according to claim 1 wherein a membrane is used through which the methanol substantially does not pass.

5. A process according to claim 4 wherein the membrane is made of polyethylene, polyvinylchloride or polyvinylidene chloride-polyvinyl chloride.

* * * * *